United States Patent [19]

Engel et al.

[11] Patent Number: 5,773,032
[45] Date of Patent: Jun. 30, 1998

[54] LONG-ACTING INJECTION SUSPENSIONS AND A PROCESS FOR THEIR PREPARATION

[75] Inventors: Jürgen Engel, Alzenau; Karin Klokkers-Bethke, Lenggries; Thomas Reissman; Peter Hilgard, both of Frankfurt, all of Germany

[73] Assignee: Asta Medica Aktiengellschaft, Dresden, Germany

[21] Appl. No.: 661,017

[22] Filed: Jun. 10, 1996

Related U.S. Application Data

[63] Continuation of PCT/EP94/03904, Nov. 25, 1994.

[51] Int. Cl.⁶ ..................................................... A61K 9/50
[52] U.S. Cl. ............................................ 424/501; 424/502

[58] Field of Search .................................... 424/489, 493, 424/501, 502; 514/772.3

[56] References Cited

U.S. PATENT DOCUMENTS

| | | |
|---|---|---|
| 4,800,191 | 1/1989 | Schally et al. . |
| 5,134,122 | 7/1992 | Orsolini . |
| 5,192,741 | 3/1993 | Orsolini et al. . |
| 5,225,205 | 7/1993 | Orsolini . |
| 5,480,656 | 1/1996 | Okada et al. ............................ 424/493 |

*Primary Examiner*—Carlos A. Azpuru
*Attorney, Agent, or Firm*—Cushman Darby & Cushman IP Group of Pillsbury Madison & Sutro LLP

[57] ABSTRACT

Poorly soluble salts of LHRH analogues, for example cetrorelix embonate, display an intrinsic sustained release effect in the grain size 5 μm to 200 μm.

8 Claims, 4 Drawing Sheets

DMBA-induced mama carcinoma
Treatment with a single dose (10 mg/kg) s.c.

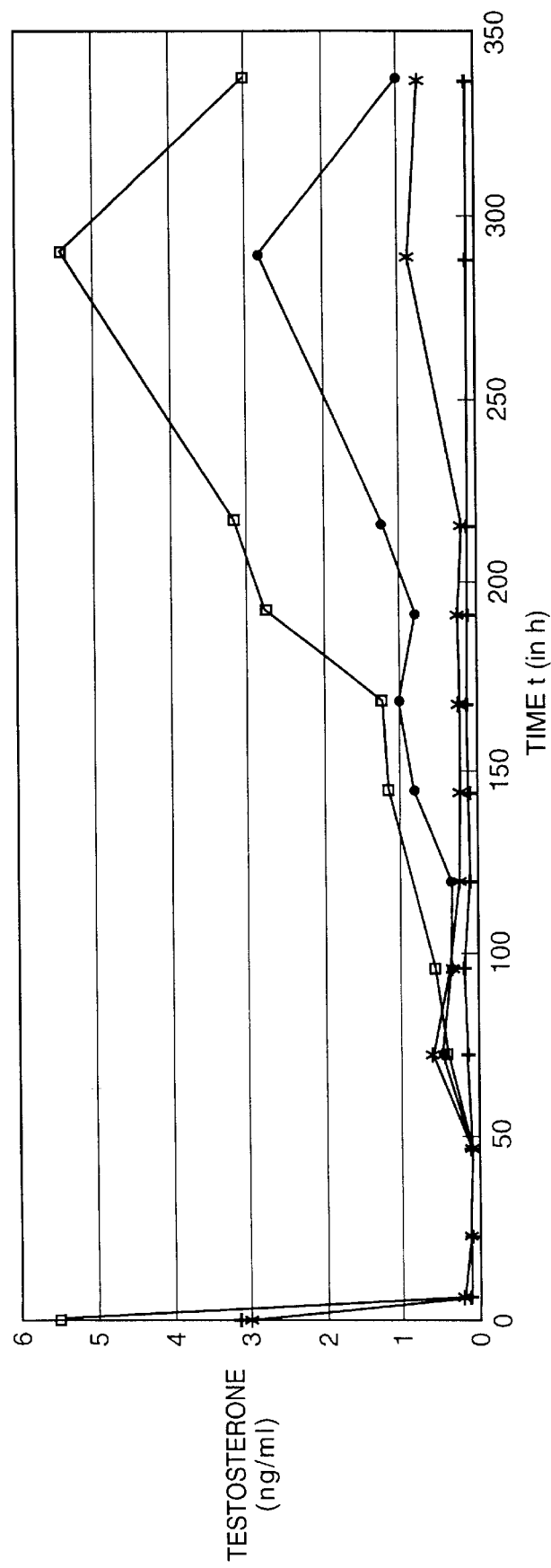

LONG-ACTING INJECTION SUSPENSIONS AND A PROCESS FOR THEIR PREPARATION

This is a Continuation of: International application No. PCT/EP94/03904 filed Nov. 25, 1994 which designated the U.S.

BACKGROUND OF THE INVENTION

1. Field of the Invention

The invention relates to long-acting injection suspensions containing therapeutically active peptides as physiologically acceptable, X-ray amorphous and crystalline salts of low solubility and to a process for their preparation.

2. Background of Information

In therapy, peptides can often only be used safely and with high bioavailability after parenteral injection since they are destroyed by enzymatic degradation after oral administration; since frequently also with nasal application only a few percent of the dosage applied are absorbed and since, with dermal application, there is no absorption at all.

Since peptides only have a very short half life in the organism, the parenteral administration of peptide medicaments, for example LHRH analogs, such as the so-called superagonists and LHRH antagonists, has to be effected daily to achieve the desired effect which consists in the case of both substance groups in the suppression of LH and FSH.

The result in men is reduction in testosterone production and, in women, in oestradiol production below a specifically defined set value. The term chemical castration is used.

LHRH analogs are understood to be both superagonists such as goserelin (INN) or triptorelin (INN), as well as antagonists such as cetrorelix (INN), antide (INN) or ganirelix (INN). Goserelin, and the synthesis of goserelin, is described in Drugs of the Future, 5 (4), (1980), p. 191. Buserelin and the synthesis of buserelin is described in Drugs of the Future, 4 (3), (1979), p. 173 and Drugs of Today, 21, (305), (1985). Decapeptyl and the synthesis of decapeptyl is described in Drugs of the Future, 3, (9), (1978), p. 645. Leuprolide and the synthesis of leuprolide is presented in Drugs of the Future 7 (12), (1982), p. 883.

Azaline B is described on pages 13–26 of GHRH-Analogues-The State of the Art (1993), Parthenon Publishing Groups Ed., B. Lunenfeld, V. Insler.

There has been no lack of attempts to process long-acting LHRH analogues in formulations having a sustained release effect. GB 2 052 258, for example, describes a formulation which contains the LHRH analogues in sustained release injection forms from the zinc salt of the peptide, sesame oil and aluminium stearate.

The difference between superagonists and antagonists lies in the fact that, in the case of superagonists, a feedback mechanism leads to the effect which is associated in the first weeks of therapy with undesired high hormone release, so-called flare up, which has to be counteracted with additional medication. In contrast, in the case of the antagonists of which cetrorelix (INN) is one, the pharmacological effect occurs immediately and there is no flare up. Lasting reduction in the sex hormone blood level is standard therapy in the palliative treatment of prostate carcinoma and mamma carcinoma to reduce tumour growth in sex hormone-dependent tumours and also a curative treatment in endometriosis. Chemically speaking, the LHRH-superagonists and the antagonists are nona-or decapeptides.

An LHRH antagonist that is effective in the above indication is cetrorelix, a decapeptide of the amino acid sequence Ac-DNal-DpCl-Phe-DPal-Ser-Tyr-DCit-Leu-Arg-Pro-D-Ala-NH$_2$. Its synthesis and pharmacological properties are described in EP 299 402. Cetrorelix acetate has been identified as the physiologically acceptable salt. It was found in preclinical and clinical studies that the aqueous solution of cetrorelix acetate had to be applied daily in order to lower the hormone level of testosterone or oestradiol to the appropriate extent until the next injection. The duration of action cannot be extended once a threshold dose was reached although a one-week instead of a daily application interval would already be a step forward for chronically sick and non-hospitalised patients.

The state of the art in the use of LHRH-analogues is the daily application of the solution of water-soluble salts as an injection solution or the multiple daily nasal use of buserelin acetate in the form of nose drops (Suprefact nasal) or of nafarelin acetate in nose drop form, which is to date only marketed in the USA. As described hereinabove, it is inherent in these medicinal forms that they have to be used frequently. Injections may only be given by a doctor, the nose drops have to be used several times daily. Both medicinal forms are poorly suited for the treatment of chronic diseases.

DE-OS 42 23 282.1 describes the preparation of a sustained release formulation of cetrorelix embonate by microencapsulation. Implants are medicinal forms permitting longer intervals of use. For example, when implanted under the skin, a cylinder of a biologically degradable poly(lactic acid-glycolic acid) copolymer containing goserelin acetate can effectively lower the testosterone level (Zoladex depot). The monthly injection of a suspension of biologically degradable polymer particles containing the active substance leuprorelin acetate also effectively lowers the sex hormone blood level over this period (Enantone Monatsdepot$^R$).

Both sustained release forms are described in the following patents or patent applications. Their obvious disadvantages, apart from the advantage of the intervals between applications, are set out hereinbelow.

EP 0 058 481 describes the composition and the preparation of implants marketed under the trademark Zoladex®. The disadvantage of the dosage form lies in the expensive process for manufacturing the cylinders using specially needed extrusion machines and the packaging machines which insert the cylinders into specially designed syringes with extremely thick cannulae. The shape of the cylinder-1 mm in diameter and several mm long—causes severe pain and haematomas when implanted into the patient A less painful dosage form is desirable.

EP 0 052 510 describes the composition and preparation of microparticles with, for example, nafarelin acetate. In the presence of chlorinated hydrocarbons the active substance is incorporated into poly(lactic acid, glycolic acid) copolymers. The use of chlorinated hydrocarbons is unavoidable in this composition since the polymers used with the biodegradation performance needed in vivo only dissolves therein. The high residual solvent contents in the medicinal form prepared in this manner of approx.=1000 ppm are a disadvantage. According to more recent knowledge, chlorinated hydrocarbons are carcinogenic, the residual solvent content in raw materials and medicaments is today limited to <50 ppm according to the current proposal for the European pharmacopoeia (Pharm Europe, Vol. 4, No. 1, March 1992). The process also has the disadvantage that the yield of active substance which is actually incorporated in microcapsules is small due to peptide losses in the aqueous phase which are essential in the process.

Reduction in residual solvent contents below this threshold value; which is desirable in the interest of drug safety, is, if at all, only possible with laborious post-treatment methods. Syntex, for example, has filed a process for residual solvent reduction with subcritical $CO_2$.

DE 40 23 134 A1 applies a similar peptide incorporation process such as described above in biologically degradable polymers of the type of poly(lactic acid, glycolic acid) copolymers. According to this application, a peptide salt insoluble in water is used instead of incorporating the peptide acetate salt in the polyester to reduce the large active substance losses in this process. Peptide salts cited as being insoluble in water are pamoates, tannates, stearates and palmitates. As already described, the process has the disadvantage that carcinogenic hydrocarbons have to be used and presents the problem of physiologically unacceptable residual chloromethane or chloroform solvent contents.

EP 145 240 contains other ways of incorporating water soluble peptide salts. In a complicated process the active substance is incorporated with marked losses in yield from aqueous active substance solution into biologically degradable poly(lactic acids, glycolic acids) copolymers via multiple emulsions, the disadvantage again being the use of chlorinated hydrocarbons.

According to EP 505 966, buserelin acetate is embedded in poly(lactic acid, glycolic acid) copolymers via the spray drying of an active substance-polymer solution containing chlorinated hydrocarbons. This process has, in turn, the disadvantage of using carcinogenic chlorohydrocarbons as solvents.

When chlorohydrocarbons are used it is not only the high residual solvent amounts in the medicinal form which are a disadvantage, but, from ecological standpoints, the use of these solvents per se, which create disposal problems for the chlorinated hydrocarbons from the manufacturing location and risks for the employees.

According to WO 9214449 readily soluble peptides such as growth hormones are incorporated in, for example, laurinic acid by mixing active substance with laurinic acid, melting down and grinding the mixture to 100 um particles after cooling. U.S. Pat. No. 5,137,669 produces sustained release forms for LHRH agonists in the same way in order to inject these particles as suspensions for delayed active substance release. A factor common to both formulations is that they need the carrier materials for the longer active substance release and only yield injectable preparations in a laborious process. It has hitherto been impossible to prove the tolerance of the fat deposits, their reliability and the reproducible release of the active substance. In the case of fat embeddings, side effects may occur at the application site in the form of encapsulations which cannot be tolerated in a chronic treatment lasting over several years.

For bromocriptine mesilate, an active substance which is very hard to prepare in sustained release form, DE 3430852 synthesises a new polyester as polyester of for example glucose with lactic acid and glycolic acid in order to achieve the desired active substance release profile. In this case it was necessary to carry out a comprehensive and costly development and toxicological trials in order to prepare a sustained release form with sufficient duration of action since it was clear that no simpler and cheaper medicinal form could achieve the same objective.

Embonic acid (4,4'-methylene-bis(3-hydroxy-2-naphtha acid) is frequently used in pharmaceutical formulations in order to formulate poorly dissolving salts of medicaments. These poorly dissolving salts therefore spend longer in the body and give the medicament a sustained release effect. (Römpps Chemie-Lexikon, Stuttgart 1976, p. 1007).

SUMMARY OF THE INVENTION

The formulation of the invention according to claim 1 was surprisingly found to cause an unexpected prolongation of action and improved effect without using biologically degradable polymers or fats. Not only was the duration of action prolonged, measured by the duration of hormone suppression, tumour growth was also found to be suppressed to a supraproportional extent.

The formulation of the invention can also be used in LHRH agonists, for example in leuprolide, buserelin, goserelin and triptorelin. The formulation of the invention may also be used in bombesin antagonists, somatostatin antagonists and GHRH analogs.

DETAILED DESCRIPTION OF THE INVENTION

The experimental procedure was conducted according to the following procedure:

Inhibitory effect on DMBA (7,12-dimethylbenz[a]-anthracene)-induced mamma carcinoma in Sprague-Dawley rats Method Female Sprague-Dawley rats (animal diet: Altromin R, water ad lib) are given 20 mg 7,12-dimethylbenz[a]-anthracene perorally dissolved in 1 ml olive oil at the age of 50 days using a stomach tube. Tumour appearance is monitored by weekly palpation of the animals. About 90% of the animals develop tumours between the 35th and 70th day after the induction which are suitable for an experimental trial.

Tumour weight was determined using the method by Druckrey, H., Steinhoff, D., Nakayama, M., Preussmann, R., Anger, K. (1983). Experimentelle Beiträge zum Dosis-Problem in der Krebs-Chemotherapie und zur Wirkungsweise von Endoxan, [Experimental contributions to the dose problem in cancer chemotherapy and to the mode of action of Endoxan], Dtsch. Med. Wschr. 88:651.

The method was validated by comparison between the tumour weights determined by palpation and the tumour weights determined by direct weighing (after tumour excision).

The correlation coefficient was 0.98. After the total weights of the tumours had reached about 1 g, the animals were randomised and 7 animals each were allocated to the control and treatment groups.

Treatment began immediately thereafter by subcutaneous injection of the test

The hormone status of the animals was determined by means of a vaginal cell smear stained with methylene blue and evaluated according to Jones, T. C., Mohr, U, Hunt, R. D. (1972): The genital system, in: Monographs on pathology of laboratory animals sponsored by the International Life Science Institute (Springer, N.Y., London).

Figure 1:
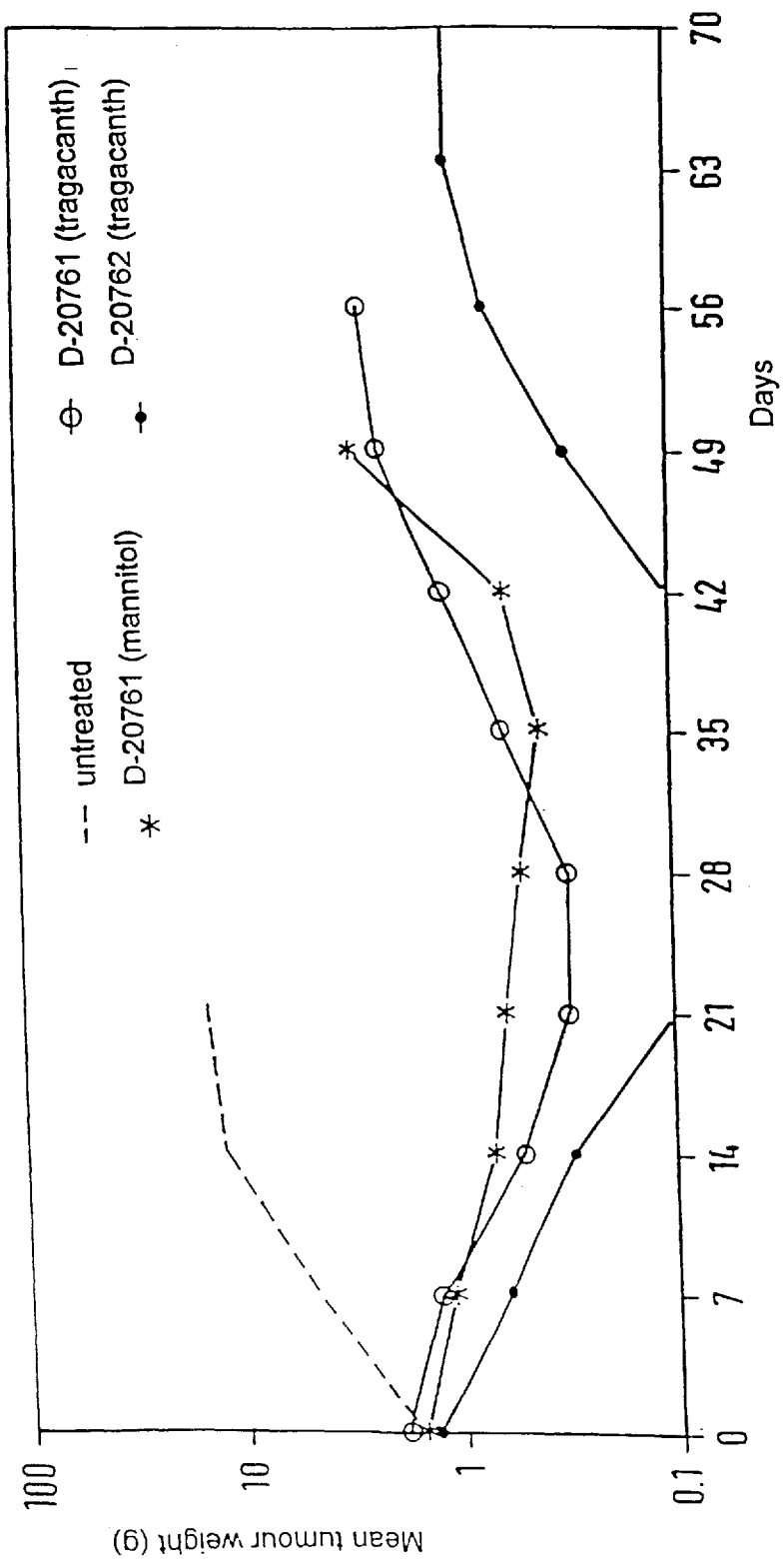
FIG. 1 DMBA-induced mamma carcinoma in female rats. Effect of treatment with a single dose of cetrorlex acetate (10 mg/kg) s.c.

The experimental results are set out in FIG. 1. The curve of the tumour weight for the untreated control animals shows uninhibited increase. Curves 1 (*) and 2 (0) show treatment with cetrorelix acetate in two different carriers. The extended curve 3 shows the drastic reduction in tumour weight after embonate treatment.

Since treatment was in this case only in a single dose, the tumour continues to grow because treatment with a single dose is not suitable for killing all tumour cells.

The formulation of the invention is an X-ray amorphous precipitate of the decapeptide cetrorelix as an embonic acid salt. The aqueous suspension of this precipitate, which may optionally contain isotonifying additives, showed a marked prolongation of action in the animal model compared to the aqueous solution of the peptide. It was surprisingly found that the duration of action was about the same as that of an injection suspension that contained the peptide embonate precipitate in a biologically degradable polymer as poly (lactic acid, glycolic acid) copolymers. This result was particularly unexpected since, as set out above, only very laboriously prepared sustained release medicinal forms, which generally contain the active substance in biologically degradable polymers, have hitherto displayed a sufficiently long duration of action.

This finding was also surprising since, according to J.Pharm Pharmavol. 47, 878–883 (1985), pyrimethamine, a 2,4-diaminopyrimidine derivative, showed no difference compared to its embonic acid salt in respect of pharmacokinetic behaviour, plasma level course and AUC after subcutaneous injection in mice. Similarly, imipramine HCl showed no difference to imipramine embonate after oral administration (Indian Journal of Physiology and Pharmacology 25, (4), 331–338 (1989). Crystalline injection suspensions of non-peptide medicinal substances such as prednisolone or triamcinolone are known in sustained release form, as in the case of the crystalline insulin zinc suspension used to treat diabetes. Insulin consists of 51 amino acids. These latter named forms are all crystalline, whereas X-ray diffractometric analysis shows the dosage form of the invention to be amorphous. The particle size of the formulation of the invention lies between 5 um and 200 um. A cetrorelix embonate with a particle size under 5 um showed a sustained release effect inferior to that of the formulation of the invention. Similarly, a cetrorelix embonate with a particle size of more than 200 um showed a poorer sustained release effect than the formulation of the invention.

Other advantages of the formulation of the invention consist in higher batch conformity: the quality of the medicament prepared with the formulation of the invention is thus subject to fewer variations.

EXAMPLE 1

In an equimolar ratio of peptide (calculated as free base) to embonic acid, an aqueous solution of embonic acid containing alkali in excess is combined with the acetate cetrorelix acetate solution, embonic acid precipitating as yellow crystals. On addition of dilute sodium hydroxide solution up to pH 7–7.5, the embonic acid dissolves and precipitates with the decapeptide as aqueous cetrorelix embonate salt of the molar composition peptide: embonic acid 2:1 (Mol/Mol). The precipitate is filtered off, washed with $H_2O$ and dried.

EXAMPLE 2

Cetrorelix acetate and embonic acid are dissolved in equimolar proportions in dimethylacetamide and the solution is dropped into water. The white precipitate of the cetrorelix embonate peptide: embonic acid 2:1 (Mol/Mol) is filtered off and dried.

EXAMPLE 3

Cetrorelix and embonic acid are dissolved in a molar ratio of 1:1.6 in a mixture of dimethyl acetamide and optionally water and the solution dropped into water. The yellow precipitate is filtered off and dried. The precipitate obtained is pasted with 70% ethanol, dried at 35° C. and sieved through a sieve of mesh size 80 to 125 um.

EXAMPLE 4

The alkaline embonate solution is added to the aqueous ethanolic solution of the peptide acetate in the molar ratio peptide: embonic acid 2:1. The white precipitate is filtered off and dried. The dried precipitate is moistened with 50% ethanol, dried in a vacuum drying cabinet and sieved. The white product contains the 2:1 peptide embonate salt (Mol/Mol).

EXAMPLE 5

The alkaline embonate solution is added to the aqueous ethanolic solution of the peptide acetate in the molar ratio peptide: embonic acid 1:1.6. The yellow precipitate is filtered off and dried. The dried precipitate is moistened with 50% ethanol, dried in a vacuum drying cabinet at 35° C. and sieved. The yellow product contains the 2:1 peptide embonate salt (Mol/Mol) in addition to the excess of embonic acid.

Experiments on duration of action in the animal

Suspensions of the precipitates were applied subcutaneously to male rats in the dose 0.5 mg cetrorelix/kg body weight and determined after application as a measure of the effect of the peptide on testosterone plasma levels. The effect of the cetrorelix consists in reduction of the testosterone level. As a reference an injection suspension was tested as well, that prepared according to DE 4023134 A1 and which contained the peptide embonate in poly(lactic acid, glycolic acid) copolymers. The duration of action of a non-sustained release dosage form of cetrorelix was determined via examination of the aqueous solution of cetrorelix acetate.

Figure 3:
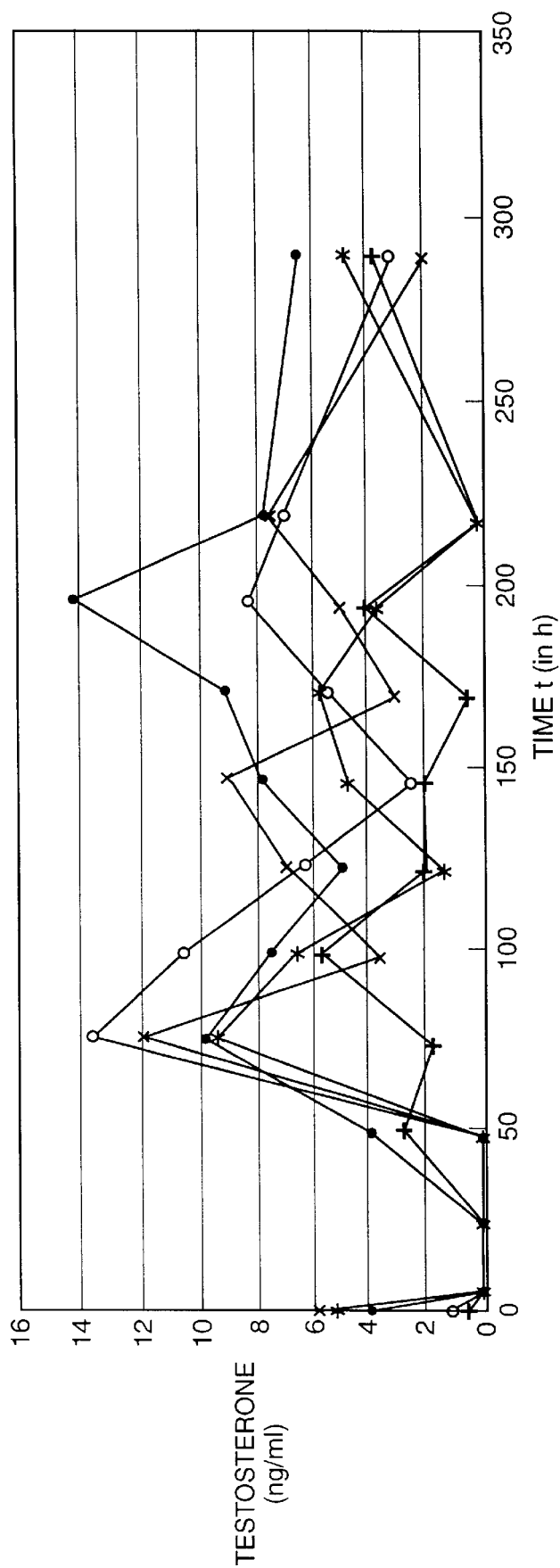
FIG. 3 Effect of administration of Cetrorelix, 0.5 mg/kg s.c. on testosterone levels in male rats. D-20762 Microparticles RCSES 91-08.

FIG. 3 shows the course of the testosterone level over 300 h determined in male rats after application of the aqueous solution of cetrorelix acetate (D-20761). The effect of testosterone suppression is achieved 6 h after the application. Suppression under 1 ng/ml could still be determined in two animals for 24 h, in three further animals up to 48 h or two days.

Figure 2:
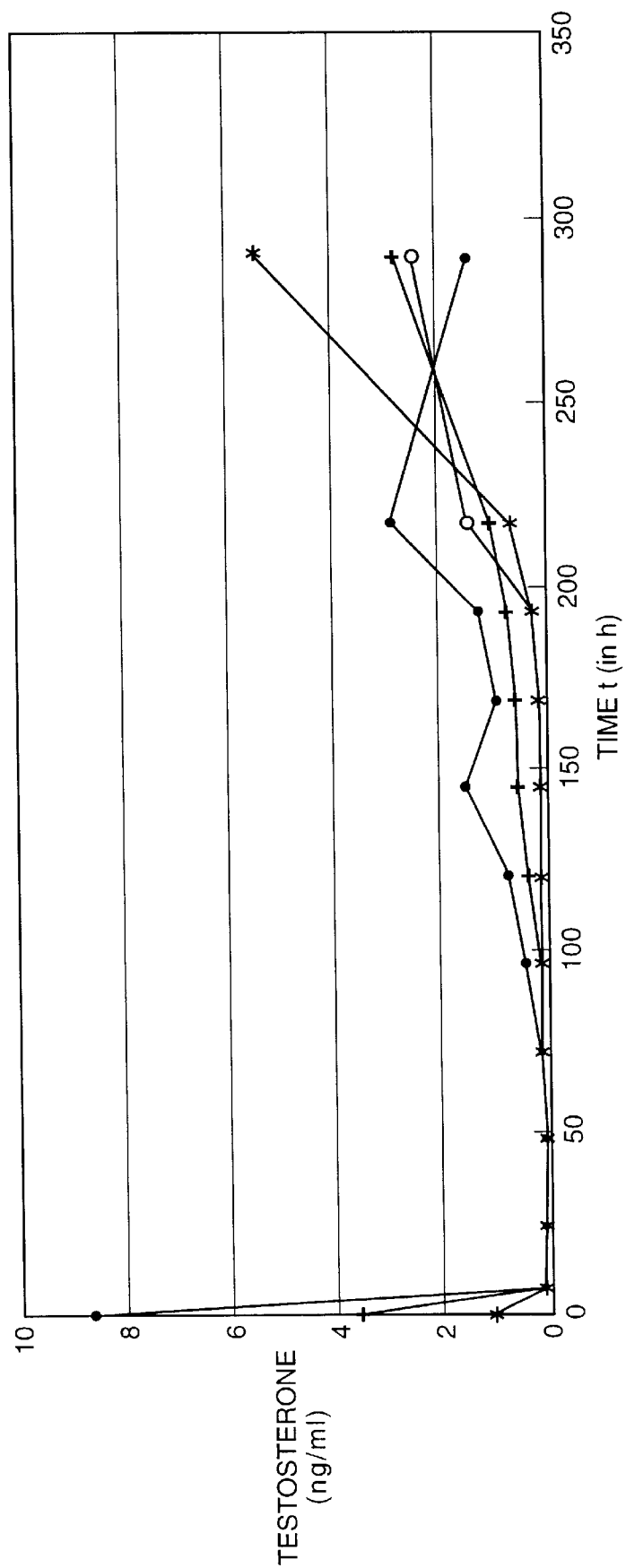
FIG. 2 Effect of administration of Cetrorelix, 0.5 mg/kg s.c. on testosterone levels in male rats. D20762 (in situ) precipitate without viscous additives.

FIG. 2 shows the testosterone level over 300 h in four animals (No. 11–14) after applying the same dose of cetrorelix as a suspension of cetrorelix embonate (D-20762) without viscous additives prepared according to Example 1 (D-20762). The testosterone suppression is also achieved 6 h after the application, the levels rise above 1 ng/ml in one animal after 192 h (eight days), in the other three animals it reliably continues until the ninth day.

FIG. 4 shows the course of the testosterone level of rats treated with the embonate of the invention (grain size: 80 um–125 um).

Comparison of FIGS. 2–3 with FIG. 4 immediately shows the advantage of the formulation of the invention.

We claim:

1. A poorly soluble salt of an LHRH analogue, wherein the particle size of the salt particles lies between 5 and 200 $\mu$m, characterized in that the LHRH analogue is selected from the group consisting of cetrorelix, antarelix, ganirelix, antide and A-75998 which is not in the form of particles or microcapsules of a homopolymer or copolymer with lactic acid and glycolic acid.

2. A salt according to claim 1, characterized in that the particle diameter of the salt particles lies between 10 and 150 µm.

3. A salt according to claim 1, characterized in that the particle diameter of the salt particles lies 20 and 125 µm.

4. A poorly soluble salt of a bombesin analogue, characterized in that the particle diameter of the salt particles lies between 5 and 200 µm.

5. A salt according to anyone of claims 1 to 4, characterized in that the salt is an embonic acid salt.

6. A pharmaceutical composition comprising a salt according to anyone of claim 1 to 5.

7. A method for producing a medicament comprising combining a salt according to one of claims 1 to 4 with a pharmaceutically acceptable carrier.

8. A method for producing a medicament comprising combining a salt according to claim 5 with a pharmaceutically acceptable carrier.

* * * * *

UNITED STATES PATENT AND TRADEMARK OFFICE
CERTIFICATE OF CORRECTION

PATENT NO. : 5,773,032
DATED      : Jun. 30, 1998
INVENTOR(S) : Engel, et al.

It is certified that error appears in the above-identified patent and that said Letters Patent is hereby corrected as shown below:

On title page, insert:

-- [30] Foreign Application Priority Data

December 9, 1993 [DE] Germany ..............43 42 092.3 --

Signed and Sealed this

Twenty-seventh Day of July, 1999

Attest:

Q. TODD DICKINSON

*Attesting Officer*     Acting Commissioner of Patents and Trademarks